(12) United States Patent
English et al.

(10) Patent No.: US 7,772,185 B2
(45) Date of Patent: Aug. 10, 2010

(54) METHOD FOR PROMOTING AXONAL OUTGROWTH IN DAMAGED NERVES

(75) Inventors: Arthur W. English, Atlanta, GA (US); Robert McKeon, Atlanta, GA (US); Erica Werner, Decatur, GA (US)

(73) Assignee: Emory University, Atlanta, GA (US)

( * ) Notice: Subject to any disclaimer, the term of this patent is extended or adjusted under 35 U.S.C. 154(b) by 256 days.

(21) Appl. No.: 11/051,996

(22) Filed: Jan. 31, 2005

(65) Prior Publication Data
US 2005/0244399 A1 Nov. 3, 2005

Related U.S. Application Data

(60) Provisional application No. 60/540,522, filed on Jan. 30, 2004.

(51) Int. Cl.
*A61K 38/51* (2006.01)
(52) U.S. Cl. ...................................................... 514/12
(58) Field of Classification Search ........................ None
See application file for complete search history.

(56) References Cited

U.S. PATENT DOCUMENTS

| | | | | |
|---|---|---|---|---|
| 5,362,641 | A | | 11/1994 | Fuks et al. |
| 5,389,539 | A | * | 2/1995 | Sasisekharan et al. ........ 435/220 |
| 5,997,863 | A | * | 12/1999 | Zimmermann et al. ...... 424/94.5 |
| 6,551,618 | B2 | | 4/2003 | Baird et al. |
| 2001/0006630 | A1 | * | 7/2001 | Yacoby-Zeevi ............. 424/93.2 |
| 2002/0068054 | A1 | | 6/2002 | Ilan et al. |
| 2003/0040112 | A1 | | 2/2003 | Muir |
| 2003/0072749 | A1 | | 4/2003 | Muir |
| 2003/0077258 | A1 | | 4/2003 | Muir |
| 2003/0091543 | A1 | | 5/2003 | Klein et al. |
| 2004/0180434 | A1 | | 9/2004 | Muir |

FOREIGN PATENT DOCUMENTS

WO WO 03/015612 A3 2/2003

OTHER PUBLICATIONS

Jackowski 1995. British Journal of Neurosurgery 9:303-317.*
Groves. Program No. 80.4 2003 Abstract Viewer/Itinerary Planner. Washington, DC:Society for Neuroscience 2003. Online.*
Alberts 1994. Molecular Biology of the Cell, 3rd Edition, pp. 128-130.*
Rudinger, In "Peptide Hormones" (ed., J.A. Parsons) University Park Press, Baltimore, pp. 1-7 (1976).*
Chuang 2002. Life Sciences 71:487-496.*
McKeon 1992. Society for Neuroscience Abstracts 18(1-2): p. 619 abstract 268.2.*
Smith-Thomas 1994. Journal of Cell Science 107:1687-1695.*
Hu 2001 (Nature Neuroscience 4:695-701).*
David, G. et al., "Developmental Changes in Heparan Sulfate Expression: In Situ Dectection with mAbs," J. Cell Biol. (Nov. 1992), p. 961-975, vol. 19, No. 4.
Desai, U.R. et al., "Substrate Specificity of the Heparin Lyases from Flavobacterium heparinum," Arch. Biochem. Biophys. (Nov. 1993), p. 461-468, vol. 306, No. 2.
Ferguson, T.A. et al., "MMP-2 and MMP-9 Increase the Neurite-Promoting Potential of Schwann Cell Basal Laminae . . . ," Mol. Cell. Neurosci. (2000), p. 157-167, vol. 16.
Gorio, A. et al., "Muscle Reinnervation Following Neonatal Nerve Crush, Interactive Effects of Glycosaminoglycans . . . ," Neuroscience (1998), p. 1029-1037, vol. 82, No. 4.
Liebl, D.J. et al., "Absence of Sensory Neurons before Target Innervationin Brain-Derived Neurotrophic Factor- . . . ," J. Neurosci. (Dec. 1997), p. 9113-9121, vol. 17, No. 23.
Lindahl, U., et al., "Regulated Diversity of Heparan Sulfate," J. Biol. Chem. (Sep. 1998), p. 24979-24982, vol. 273, No. 39.
Stoll, G. et al., "Nerve Injury, Axonal Degeneration and Neural Regeneration: Basic Insights," Brain Pathology (1999), p. 313-325, vol. 9.
Tabb, J.S. et al., "Suppression of Sodium Channel Function in Differentiating C2 Muscle Cells Stably Overexpressing . . . ," J. Neurosci. (Feb. 1994), p. 763-773, vol. 14, No. 2.
Tona, A. et al., "Extracellular Matrix in Regenerating Rat Sciatic Nerve: A Comparitive Study . . . ," J. Histochem. Cytochem. (1993), p. 593-599, vol. 41, No. 4.
Trigg, D.J. et al., "Peripheral Nerve Regeneration: Comparison of Laminin and Acidic Fibroblast Growth Factor," Amer. J. Otolaryngology (1998), p. 29-32, vol. 19, No. 1.
Groves, M. et al., "Axon regeneration in peripheral nerves is enhanced by proteoglycan degradation," *Experimental Neurology*, 2005, pp. 278-292, vol. 195.
Yick, L. et al., "Axonal regeneration of Clarke's neurons beyond the spinal cord injury scar after treatment with chondroitinase ABC," *Experimental Neurology*, vol. 182, Jul. 2003, pp. 160-168.
Zuo, J. et al., "Regeneration of Axons after Nerve Transection Repair is Enhanced by Degradation of Chondroitin Sulfate Proteoglycan," *Experimental Neurology*, Jan. 2002, vol. 176, pp. 221-228.

\* cited by examiner

*Primary Examiner*—Daniel E. Kolker
(74) *Attorney, Agent, or Firm*—Saliwanchik, Lloyd & Saliwanchik

(57) ABSTRACT

The subject invention pertains to the therapeutic use of certain GAG-degrading enzymes, and enzyme combinations, to promote nerve repair and regeneration.

14 Claims, 8 Drawing Sheets

METHOD FOR PROMOTING AXONAL OUTGROWTH IN DAMAGED NERVES

CROSS-REFERENCE TO A RELATED APPLICATION

This application claims the benefit of U.S. provisional patent application Ser. No. 60/540,522, filed Jan. 30, 2004.

GOVERNMENT SUPPORT

The subject matter of this application has been supported in part by U.S. Government Support by NICHD under Grant No. HD32571. Accordingly, the U.S. Government has certain rights in this invention.

BACKGROUND OF THE INVENTION

Nerve injuries are a major source of chronic disability. Poor management of nerve injuries is associated with muscle atrophy and can lead to painful neuroma when severed axons are unable to reestablish continuity with the distal nerve. Although nerves have the potential to regenerate after injury, this ability is strictly dependent upon the regenerating nerve fibers (and their axonal sprouts) making appropriate contact with the severed nerve segment (and the Schwann cell basal laminae therein). Regenerating axons that fail to traverse the gap or injury site and enter the basal lamina of the severed distal nerve segment will deteriorate, resulting in neuronal death, muscle atrophy and permanent functional deficit (Fawcett J W et al. [1990] *Annu Rev Neurosci* 13:43-60).

Briefly, a nerve carries the peripheral processes (or axons) of neurons. The neuronal cell bodies reside in the spinal cord (motor neurons), in ganglia situated along the vertebral column (spinal sensory ganglia) or in ganglia found throughout the organs of the body (autonomic and enteric ganglia). A nerve consists of axons, Schwann cells and extensive connective tissue sheaths (Dagum A B [1998] *J Hand Ther* 11:111-117). The outer covering, the epineurium, is made of collagenous connective tissue that cushions the fascicles from external pressure and surrounds the perineurium. The perineurium surrounds the individual fascicles and, together with endothelial cells in the endoneurial microvessels, functions as the blood-nerve barrier. The endoneurium lies inside the perineurium and consists of collagenous tissue that surrounds the Schwann cells and axons. A fascicular group consists of two or more fascicles surrounded, respectively, by perineurium and epineurium. The topography of nerves is constant distally, with a group of fascicles being either sensory or motor. The neuron consists of a soma (cell body) and an axon, which can be several feet long.

In nerve injuries where there is axonal disruption, but the continuity of the endoneurial sheath remains intact (e.g., crush injury), axons regenerate within their original basal lamina and complete recovery can be expected. In contrast, axonal regrowth may be severely compromised after nerve transection and surgical repair is highly dependent on the realignment of the nerve elements described above (Dagum A B [1998] *J Hand Ther* 11:111-117).

Complete regeneration of axons in damaged peripheral nerves is rare. For axon regeneration to occur, regenerative sprouts must enter endoneurial tubes in the distal stump of the nerve (Tona A, Perides G, Rahemtulla F, Dahl D [1993] *J Histochem Cytochem* 41:593-599; Stoll G, Muller H W (1999) *Brain Pathology* 9:313-325) where they encounter growth promoting molecules, such as laminin and fibronectin, (Tabb J. S. et al. (1994) *J Neurosci* 14:763-773; Gorio, A. et al. (1998) *Neuroscience* 82:1029-1037; Trigg, D. J. et al. (1998) *Amer J Otolaryngol* 19:29-32; Ferguson, T. A. and D. Muir (2000) *Mol Cell Neurosci* 16:157-167), as well as molecules that inhibit growth. If the neurons do not make this contact with the distal stump, they will form a neuroma and their growth is disorganized (Sunderland (1978) Fu S Y, Gordon T (1997) *Mol Neurobiol* 14:67-116.).

Some use of growth factors, to stimulate axon elongation has been used in laboratory animals. The different growth factors act by binding to specific cell surface receptors on neurons, and the different receptors are not found on all neurons in peripheral nerves, only in subsets of them. The major disadvantage of the use of growth factors to promote axon regeneration is this heterogeneity. Not surprisingly, specific growth factors will, at best, promote the outgrowth of axons from only a subset of neurons. The use of nerve growth factor (NGF) in a recent clinical trial illustrates this point. The receptor for NGF, trkA, is found largely on sensory neurons that convey information about painful stimuli. Treatment of patients with diabetic peripheral neuropathy with NGF resulted in a hyperalgesia, an increased sensitivity to painful stimuli, without significant restitution of function of other neuronal types.

Thus, although axons of peripheral nerves can regenerate after being damaged, optimal axonal regeneration in the peripheral nervous system rarely occurs. If endoneurial tubes surrounding individual axons and their ensheathing myelin are damaged beyond repair, there is often little axon regeneration.

At present there are no clinically used therapeutic methods to enhance axon regeneration in peripheral nerves.

BRIEF SUMMARY OF THE INVENTION

The subject invention provides compositions and methods for promoting the repair and/or growth of nerve tissue. In a preferred embodiment, the methods of the subject invention comprise administering a heparan sulfate proteoglycan (HSPG)-degrading enzyme to an injured nerve.

Methods of the present invention include administering one or more HSPG-degrading enzymes to a nerve repair, coaptation, graft, or damaged nerve tissue. The methods of the subject invention improve the ability of regenerating axons to traverse the nerve-nerve or nerve-graft interface and potentiate axonal growth.

One embodiment of the subject invention comprises the use of an HSPG-degrading enzyme such as heparinase I, heparinase III, heparanase, or a matrix metalloproteinase (MMP), or combinations thereof for nerve repair. The subject invention further provides methods for enhancing nerve regeneration comprising administering an HSPG-degrading enzyme such as heparinase in combination with one or more other enzymes to nerves, or their situs. For example, one embodiment the subject invention contemplates the use of an HSPG-degrading enzyme used together with a chondroitin sulfate proteoglycan (CSPG)-degrading enzyme. The CSPG-degrading enzyme may be, for example, chondroitinase ABC, chondroitinase A, chondroitinase C, chondroitinase AC, hyaluronidase, MMP-2 or MMP-9, or combinations thereof. Other agents, such as hyaluronidase, which affect the biological activity of HSPGs may also be used in accordance with the subject invention.

In a preferred embodiment, the invention provides methods for enhancing peripheral nerve regeneration by administering a combination of heparinases and one or more CSPG-degrading enzymes, and/or other GAG-degrading enzymes. For example, the invention provides methods for enhancing peripheral nerve regeneration by administering heparinase I, heparinase III and chondroitinase ABC to peripheral nerves. The invention also contemplates methods for enhancing nerve regeneration comprising administering a combination of heparinase with one or more matrix metalloproteases.

The present invention also concerns methods of preparing nerve grafts by treatment with HSPG-degrading enzymes. The present invention also concerns methods of culturing fresh (or briefly preserved for transport) nerve tissue for subsequent implantation as a nerve graft into a human or animal. The present invention further pertains to methods of providing nerve grafts for implantation into humans or animals.

Heparinases are well known to those skilled in the art and are commercially available. Other enzymes useful according to the subject invention are also commercially available. The methods and compositions of the present invention contemplate both wild-type enzymes as well as variants. The methods and compositions of the invention contemplate, for example, the use of heparinases derived from any plant, animal, or microbial source, including fungi, yeast, and bacteria. In particular, the methods and compositions of the invention comprise heparinases that are classified under the EC numbers 4.2.2.7. and 4.2.2.8.

BRIEF DESCRIPTION OF THE FIGURES

FIG. 1A was constructed from six images at the same optical section plane through the $L_4$ dorsal root ganglion of a thy-1-YFP-H mouse. Fluorescent axons are visible in the dorsal and ventral roots at the proximal end of this ganglion and in the $L_4$ spinal nerve at the distal end of the ganglion. In FIG. 1B, the distribution of soma cross sectional areas of YFP$^+$ and surrounding YFP$^-$ neurons are shown for the L4 dorsal root ganglion of a single mouse (left). The mean soma areas of these two groups (+SEM) from all of the ganglia studied are shown to the right.

In FIG. 2A, the experimental paradigm used is shown. The common fibular nerve of thy-1-YFP-H mice was cut (left) and repaired using a graft from the same nerve in a wild type littermate. On one side of each animal, the graft was soaked for an hour at room temperature (23° C.) in an enzyme solution. On the other side of each mouse the graft was soaked in normal saline. In FIG. 2B, images are shown from a single optical section taken through the nerves and saline-(above) or chondroitinase ABC-treated (below) graft. The images were obtained from adjacent microscope fields and stitched together to reconstruct the nerve and graft. Arrows in the two panels point to the location of the proximal attachment of the graft. In the saline treated graft, this optical section contained no long regenerating axons. In FIG. 2C-F, higher magnification images are shown of the endings of axon profiles in the saline-treated (2C) and chondroitinase-treated (2D-F) grafts.

In FIG. 3A, the distribution of axon profile lengths measured in saline—(filled bars) and chondroitinase ABC-treated (open bars) grafts is shown. Data are shown for a single mouse, one week following transection and surgical repair of the common fibular nerve. Note that a population of axon profile lengths longer than 1500 µm is found only among axons growing in the chondroitinase treated grafts (bracket). In FIG. 3B, the distribution of axon profile lengths is displayed as cumulative frequency plots. Data points in this graph represent the means (±SEM) of six mice treated either with saline (heavy line) or chondroitinase ABC (fine line).

In FIG. 4C, the distribution of axon profile lengths measured in grafts treated with a combination of all of the enzymes (thin black line) is shown in comparison to the data from saline-treated grafts (thick line) and the arithmetic sum of the effects of treatments with individual enzymes (thin grey line). Each data point on each line represents the mean from five mice. Error bars are SEM in panels A and B, and 95% confidence limits in panel C.

In FIG. 5A, the bars represent the mean (±SEM) percentage of axon profiles longer than 500 µm found for each of the four enzyme treatments used, for a group of mice in which the common fibular nerve was repaired with an untreated graft, and for the saline treatment of grafts. In FIG. 5B, the bars represent the average (±SEM) length of axons >500 µm long in the same groups.

In FIG. 8A, the immunoreactivity to antibody 3G10 is shown in transverse sections through mouse common fibular nerves pre-treated with heparinase III. No immunoreactivity is found after heparinase I (FIG. 8B), chondroitinase ABC (FIG. 8C), or saline (FIG. 8D) pre-treatment. Scale Bar=20 µm.

DETAILED DESCRIPTION OF THE INVENTION

Figure 1:
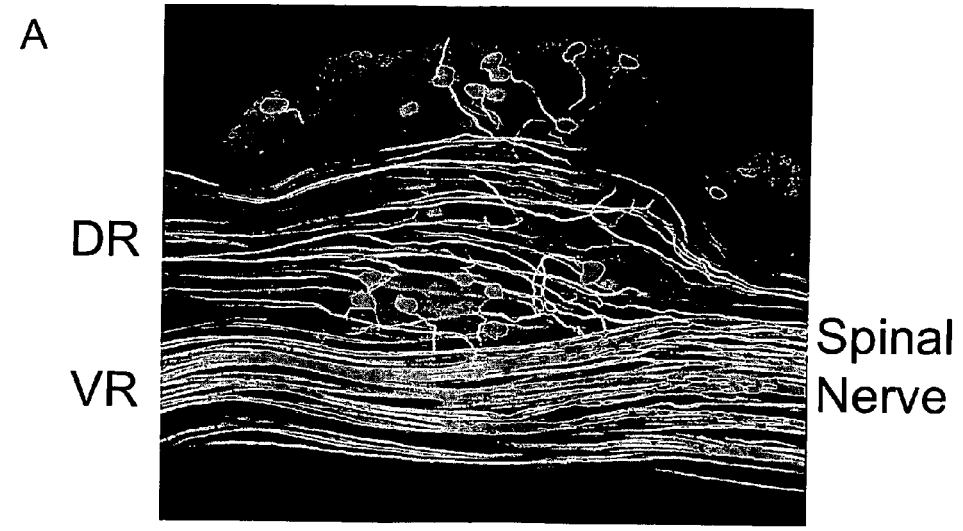
FIGS. 1A-1B.
Figure 1:
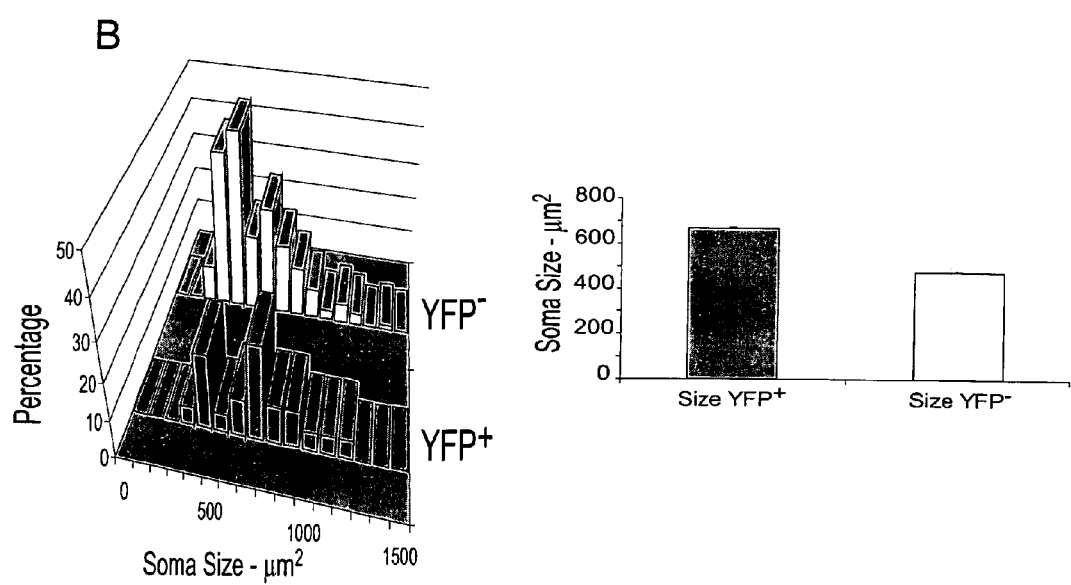

The subject invention provides compositions and methods for promoting the repair and/or growth of nerve tissue. The compositions and methods of the subject invention can be employed to restore the continuity of nerves interrupted by disease, traumatic events or surgical procedures. The compositions and methods of the subject invention promote repair of nerve tissue by increasing the number of axons that successfully penetrate damaged nerve tissue or implanted nerve grafts, resulting in greater functional recovery.

Following peripheral nerve injury, if axons in the proximal stump are to regenerate and reinnervate their targets successfully, they need to select a pathway in which to grow. This process of pathway selection involves the navigation of regenerating axons in the proximal stump past the surgical repair site and into endoneurial tubes in the distal stump.

In a specific embodiment described more fully herein, heparinase can be used according to the subject invention to treat injured nerves and promote nerve repair. In accordance with the subject invention, application of heparinase to the repair site of a cut peripheral nerve at the time of injury produces a striking enhancement of axonal regeneration. In particularly preferred embodiments, heparinase is applied in conjunction with one or more additional enzymes. Specifically exemplified herein is the combined use of heparinases and chondroitinase ABC to promote the repair of peripheral nerves.

The effects of enzymatic treatment on the regeneration of peripheral axons were compared as described herein. Specific enzymes whose activities are described and exemplified herein are heparinase I, heparinase III, chondroitinase ABC, and keratanase. Common fibular (CF) nerves of thy-1-YFP-H mice were cut and repaired using short segments of CF nerves harvested from wild type littermates and pre-treated with a GAG-degrading enzyme for one hour prior to nerve repair. Axonal regeneration was assayed by measuring the lengths of profiles of axons in optical sections of the grafted nerves one week later. Except for grafts treated with keratanase, more axon profiles longer than 500 µm were encountered in enzyme treated grafts than in control grafts.

In this analysis, it was assumed that the process of regenerative pathway selection was successful if an axon had grown at least 500 µm into a graft during the one week survival period. In the nerve grafts used to repair cut peripheral nerves, significantly more axons had grown this distance if the pathway through which the regenerating axons grew was treated with chondroitinase ABC, heparinase I, or heparinase III.

Thus, in accordance with the subject invention, in nerve grafts used to repair cut peripheral nerves, significantly more axons that had grown more than 500 µm were encountered one week after repair if the pathway through which the regenerating axons grew was treated with heparinase or chondroitinase than if it had been soaked in normal saline or was untreated. Treatments with heparinase I combined with chondroitinase ABC were particularly effective in helping regenerating axons find a suitable environment in which to grow.

Treatment with a mixture of all four enzymes (heparinase I, heparinase III, chondroitinase ABC, and keratanase) resulted in an enhancement of axon regeneration that was greater than that observed after treatment with any of the enzymes individually.

While chondroitinase ABC, heparinase I, and heparinase III treatments each produce an enhancement of axon regeneration, the manner in which this enhancement is expressed differs slightly for each of the treatments.

Following peripheral nerve injury, one of the earliest aspects of the process of axon regeneration is the formation of regenerative sprouts. Individual cut axons in the proximal stump give rise to new neuritic processes. In grafts treated with heparinase I, nearly twice as many regenerative sprouts form after heparinase I treatment as with any other treatment.

Once a pathway has been selected for regeneration, axons must elongate in that pathway. The mean lengths of those axon profiles longer than 500 µm measured in chondroitinase-treated grafts and in grafts treated with heparinase I, were significantly greater than found in grafts treated with keratanase, heparinase III, or saline, or in untreated grafts. Consequently, heparinase III does not appear to enhance axon regeneration by stimulating the axons to elongate more rapidly, only by enhancing the ability of the axons to enter the regeneration pathway in the graft.

Heparinase I and heparinase III are bacterial lyases which degrade the GAGs on HSPGs. Using antibody 3G10, which binds to linkage regions of HSPG core glycoproteins that are exposed by heparinase III treatment (David G, Bai X M, Van der Schueren B, Cassiman J J, Van den Berghe H (1992) "Developmental changes in heparan sulfate expression: in situ detection with mAbs" *J Cell Biol* 119:961-975), strong endoneurial immunoreactivity was found after heparinase III, but not heparinase I treatment.

In accordance with the subject invention, enzymatic removal of GAGs is especially effective in promoting the ability of regenerating axons to select their pathway in the distal stump (or nerve graft) and, in the case of chondroitinase ABC or heparinase I, it can also promote growth within that pathway. Thus, in one embodiment, the subject invention provides materials and methods for nerve regeneration utilizing HSPG-degrading enzymes in combination with other GAG-degrading enzymes such as KSPG-degrading enzymes or DSPG-degrading enzymes. Thus, keratanase and/or endo-b-galactosidase can be used according to the subject invention.

The HSPG-degrading enzymes used according to the subject invention can be human, animal, or bacterial in origin, naturally occurring or recombinant. As used herein, the term "HSPG-degrading enzymes" is also intended to include biologically active fragments and variants of such enzymes, e.g., that retain HSPG-degradative activity. This same definition applies to CSPG-degrading enzymes. In this regard the teachings of US-2003-0072749-A1; US-2003-0077258-A1; US-2003-0040112-A1; US-2004-0180434-A1; and WO 2003/015612 A3 are hereby incorporated herein by reference in their entirety. The compositions of the subject invention can include an appropriate pharmaceutical carrier and other active agents.

In addition to one or more HSPG-degrading enzymes, the compositions of the subject invention can further comprise biologically or pharmacologically active molecules, such as growth factors. Such growth factors include, but are not limited to, nerve growth factor (NGF), fibroblast growth factors (FGF-1 and 2), epidermal growth factor (EGF), ciliary neurotrophic factor (CNTF), brain derived neurotrophic factor (BDNF), neurotrophin-3,-4, and -5 (NT-3,-4, and -5), insulin-like growth factor-I and -II (IGF-I, II), transforming growth factor (TGF), glial growth factor-2 (GGF-2), vascular endothelial growth factor (VEGF), granulocyte-macrophage colony stimulating factor (GM-CSF), and lymphocyte infiltrating factor/cholinergic differentiating factor (LIF/CDF). Such molecules can be obtained naturally or by recombinant DNA techniques. Fragments or variants of such molecules that retain their biological or pharmacological activities can also be used.

Application of HSPG-Degrading Enzymes to Damaged Nerve. In one embodiment, the HSPG-degrading enzymes are applied to damaged nerve, the site of nerve damage or the site of nerve damage repair. In a preferred embodiment, the HSPG-degrading enzymes are applied to the site of primary nerve repair involving coaptation of severed or trimmed nerve (i.e., end-to-end nerve coaptation). The damage to the nerve can represent a nerve transection (neurotmesis), wherein the nerve is partially or fully severed or a small region damaged and surgically removed, and epineurial coaptation (neurorrhaphy) is the primary method of repairing the damaged nerve. For example, the compositions and methods of the subject invention can be used to promote repair of nerve damage that involves a disruption in the continuity of at least one of the nerve sheaths of the damaged nerve, such as the basal lamina, perineurium, or epineurium. Preferably, the surgical repair attempts to realign nerve elements.

In a specific embodiment, the damage to the nerve represents a nerve crush injury (axonotmesis) or more extreme damage, where there is axotomy but the continuity of the sheath remains intact or is somewhat compromised. In the case of axonotmesis, axons typically regenerate without surgical intervention.

In some cases, a segment of the nerve is diseased, irreparably damaged or obliterated and is surgically removed. Repair may involve implantation of a graft or prosthesis to bridge the gap. The implant may be natural (e.g., nerve or vascular graft), a natural derivative (e.g., biopolymer tube) or synthetic conduit (e.g. silicone tube). These are connected to the cut nerve ends. In a specific embodiment, the HSPG-degrading enzyme(s) is applied at the connection sites, at either or both ends. For example, the HSPG-degrading enzyme(s) can be applied to one or both points of host-graft interface on an interpositional graft. The HSPG-degrading enzyme(s) can be applied before, during, or after surgical repair of the damaged nerve tissue or implantation of the graft within the recipient. In one embodiment, the enzyme(s) is applied to the damaged area using the implant. The implant may be, for example, the nerve graft or even a synthetic nerve conduit.

Application of HSPG-Degrading Enzymes to Nerve Grafts. In one embodiment, the HSPG-degrading enzyme is applied to a nerve graft. When the HSPG-degrading enzyme(s) is applied to a nerve graft, the entire graft can be treated. HSPG-degrading enzymes can be applied to the entire nerve graft, en bloc. This application is a pretreatment or incubation prior to implantation and may or may not involve procedures to remove the applied enzyme.

According to the methods of the subject invention, the HSPG-degrading enzyme(s) can be applied to the nerve graft or damaged nerve tissue, or both. The HSPG-degrading enzyme(s) can be applied to a nerve graft before, during, or after implantation. The HSPG-degrading enzyme(s) can be placed in a culture medium for application to the nerve graft.

As used herein, the term "graft" refers to any tissue intended for implantation within a human or animal. Various types of graft are encompassed within the subject invention, such as autografts, syngrafts, allografts, and xenografts. The size (e.g., length and diameter) of the graft is not critical to the subject invention. The graft may be a live (cellular) graft or a graft that has been rendered acellular, such as by chemical or thermal decellularization methods.

Optionally, the HSPG-degrading enzyme can be applied to the injured nerve or nerve graft in conjunction with a tissue adhesive, such as a biological glue. Preferably, the biological glue is a fibrin-containing adhesive, such as fibrin glue, fibrin sealant, or platelet gel. As used herein, the terms "fibrin glue", "fibrin sealant", and "fibrin tissue adhesive" are used interchangeably to refer to a group of formulations containing fibrinogen and thrombin, which lead to the formation of a fibrin clot at the site of application. The tissue adhesive can be applied simultaneously or consecutively with the HSPG-degrading enzyme.

The HSPG-degrading enzymes used in the subject invention can be applied to the nerve graft or damaged nerve tissue by various means and in a variety of formulations. As used herein, the terms "applied", "administered", "contacted", and "treated" are used interchangeably. For example, the HSPG-degrading enzymes can be applied to the nerve graft or damaged nerve tissue topically (e.g., drop-wise), or administered by injection. Topical application or local administration by injection are preferred for greater control. Further, the HSPG-degrading enzymes, or compositions containing such enzymes, are preferably applied as a liquid, flowable, formulation. The HSPG-degrading enzyme or enzymes can also be adsorbed onto a porous substance, or formulated into an ointment, salve, gel, cream, or foam, for example.

The subject invention also includes kits for promoting repair of damaged nerve tissue. The kits of the invention include a first compartment containing at least one HSPG-degrading enzyme and a second compartment containing a tissue adhesive, such as those described herein. Optionally, the kits can include a third compartment for mixing the HSPG-degrading enzyme or enzymes and the tissue adhesive. The kits can be used for repair of damaged nerve tissue directly, or indirectly, via nerve graft. The kit can include packaging of various materials known in the art, such as plastic, glass, and/or paper products.

Pharmaceutical Compositions. One or more HSPG-degrading enzymes can be incorporated into a pharmaceutical composition suitable for administration to a patient, e.g., a human or animal. Such compositions typically comprise at least one HSPG-degrading enzyme and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

The pharmaceutical compositions of the subject invention can be formulated according to known methods for preparing pharmaceutically useful compositions. For further detail refer to, for example, WO 2003/015612, which is incorporated herein by reference in its entirety. Formulations are described in a number of sources which are well known and readily available to those skilled in the art. For example, *Remington's Pharmaceutical Science* (Martin E W [1995] Easton Pa., Mack Publishing Company, $19^{th}$ ed.) describes formulations which can be used in connection with the subject invention.

The HSPG-degrading enzymes can be formulated in a carrier appropriate for the mode of administration, e.g., saline or aqueous buffer. The HSPG-degrading enzymes can also be contained within, or associated with, a controlled release formulation.

The HSPG-degrading enzymes can be prepared with carriers that will protect the enzymes against rapid elimination from the body, such as a controlled release formulation, including implants and microencapsulated delivery systems.

U.S. Pat. No. 5,320,837 describes controlled release preparations obtained by reacting an enzyme having an amino group, such as hyaluronidase or chondroitinase, with a copolymer of maleic anhydride and a copolymerizable polyalkylene glycol ether.

U.S. Pat. No. 4,933,185 describes a controlled release system for delivery of a biologically active substance consisting of an enzyme (such as hyaluronidase) encapsulated within a microcapsule having a core formed of a polymer, such as an. ionically cross-linked polysaccharide, which is specifically degraded by the enzyme and a rate controlling skin. The integrity of the skin is lost when the core is degraded, causing a sudden release of the biologically active substance from the capsule. The controlled release system in the '185 patent can be utilized to deliver a HSPG-degrading enzyme or enzymes. For example, the HSPG-degrading enzyme or enzymes can function as the biologically active substance, or the core degrading enzyme, or both.

The controlled release formulation can provide an initial exposure of the HSPG-degrading enzyme or enzymes, followed by one or more delayed exposures following a specific period of time. Alternatively, the controlled release formulation can cause a single delayed release of the HSPG-degrading enzyme or enzymes. Alternatively, the continuous release formulation can allow for continuous release of the HSPG-degrading enzyme or enzymes. Optionally, the continuous release of the HSPG-degrading enzyme or enzymes can be in conjunction with one or more pulsed releases.

The carrier of the HSPG-degrading enzymes, such as an implant, can be of a size and shape appropriate for the particular application. Thus, the carrier can be of a desired volume and in a desired shape, designed in due consideration of the region of the living body at which the carrier is put to use.

The amount of HSPG-degrading enzyme or enzymes released from the carrier and the duration of release can be controlled within appropriate ranges. The carrier can be fixed or secured to the graft or injured nerve or to tissue adjacent to the graft or injured nerve. The carrier can continuously release the HSPG-degrading enzyme or enzymes at the nerve injury site over a period of time, such as, for example, 24 hours to three months.

Depending upon the particular carrier utilized, the HSPG-degrading enzyme or enzymes can be contained within, coated, or otherwise associated with the carrier during or after its manufacture. For example, the HSPG-degrading enzyme or enzymes can be associated with a commercial product.

The carrier can also function to deliver other biologically active agents, such as cells (e.g., Schwann cells) or growth factors, with the HSPG-degrading enzymes. The cells delivered by the carrier can be derived from the patient, or from another source of the same species or a different species. The cells delivered by the carrier can be genetically modified to produce a biologically active agent.

In one embodiment, the carrier is a surgical cuff, such as those described in U.S. Pat. No. 4,602,624, U.S. Pat. No. 5,487,756, and published U.S. Patent Application No. 2002/0071828, which can be implanted closely adjacent to the nerve graft or injured nerve (e.g., at the site of damage). Optionally, the cuff can include a means for electrically stimulating the nerve graft or damaged nerve and/or a means for recording nerve electrical activity within the nerve graft or damaged nerve, such as that described in U.S. Pat. No. 5,487,756. Preferably, the HSPG-degrading enzyme or enzymes are released or otherwise operate from the inner surface of the cuff, i.e., that surface facing the nerve graft or damaged nerve.

The surgical cuff can provide the HSPG-degrading enzyme or enzymes to the nerve graft or damaged nerve via a delivery system, such as a reservoir or an expression system, such as the adenovirus constructs described in published U.S. Patent Application No. 2002/0071828. Expression systems for chondroitin lyase enzymes are known in the art, some of which are described in U.S. Pat. No. 6,054,569; U.S. Pat. No. 6,093,563; published U.S. Patent Application No. 2001/0034043; and Tralec, A. L. [2000] *Appl. Environ. Microbiol.* 66:29-35.

The HSPG-degrading enzymes can be applied to the nerve graft or damaged nerve tissue in various concentrations, but are preferably applied in a concentrated form. Ideal concentrations will vary with nerve size and enzyme. Heparinases can be applied in a concentration ranging from about 10 units/mL to about 100 units/mL. Preferably, the heparinases are applied to the nerve graft or damaged nerve tissue at a concentration range from about 10 units/mL to about 50 units/mL. For example, chondroitinase can be applied in a concentration ranging from about 10 units/mL to about 1000 units/mL. Preferably, the chondroitinase is applied to the nerve graft or damaged nerve tissue at a concentration range from about 100 units/mL to about 500 units/mL. MMPs can be applied in a concentration ranging from about 0.1 µg/mL to about 100 µg/mL. Preferably, the MMP is applied in a concentration ranging from about 10 µg/mL to about 50 µg/mL.

As indicated above, according to the methods of the subject invention, the HSPG-degrading enzyme or enzymes can be administered to a nerve graft or injured nerve tissue in conjunction with a biologically active molecule, such as a growth factor. Other biologically active agents that can be administered with the HSPG-degrading enzyme or enzyme include genetically-modified or non-genetically modified cells. Thus, the compositions of the subject invention can include such cells. The cells can be non-stem cells (mature and/or specialized cells, or their precursors or progenitors) or stem cells. For further detail refer to, for example, WO 2003/015612, which is incorporated herein by reference in its entirety.

Stem cells can be obtained from a variety of sources, including fetal tissue, adult tissue, cord cell blood, peripheral blood, bone marrow, and brain, for example. Stem cells and non-stem cells (e.g., specialized or mature cells, and precursor or progenitor cells) can be differentiated and/or genetically modified.

According to the methods of the subject invention, genetically modified hosts, such as recombinant cells, can be administered to the nerve graft or damaged nerve tissue. The hosts can be genetically modified to produce one or more HSPG-degrading enzymes. Preferably, the HSPG-degrading enzyme is secreted from the recombinant cell. For example, expression systems for enzymes are known in the art, some of which are described in U.S. Pat. No. 6,054,569; U.S. Pat. No. 6,093,563; published U.S. Patent Application No. 2001/0034043; and Tralec, A. L. [2000] *Appl. Environ. Microbiol* 66:29-35. Optionally, the recombinant host is genetically modified to recombinantly produce other biologically active agents, in addition to the HSPG-degrading enzyme.

Nucleic acid molecules encoding one or more HSPG-degrading enzymes can be inserted into vectors and used as gene therapy vectors. Gene therapy vectors can be delivered to a patient by, for example, intravenous injection, local administration, or by stereotactic injection. The pharmaceutical preparation of the gene therapy vector can include the gene therapy vector in an acceptable diluent, or can comprise a slow release carrier in which the gene delivery vehicle is imbedded or otherwise associated. In addition, the pharmaceutical preparation can include a therapeutically effective amount of cells which recombinantly produce the HSPG-degrading enzyme.

The various methods employed in the genetic modification of host cells are well known in the art and are described, for example, in Sambrook et al. (1989) *Molecular Cloning: A Laboratory Manual*, second edition, volumes 1-3, Cold Spring Harbor Laboratory, New York, and Gloves, D. M. (1985) *DNA Cloning, Vol. I.: A Practical Approach*, IRL Press, Oxford. Thus, it is within the skill of those in the genetic engineering art to extract DNA from its source, perform restriction enzyme digestions, electrophorese DNA fragments, tail and anneal plasmid and insert DNA, ligate DNA, transform cells, e.g., prokaryotic and eukaryotic cells, prepare plasmid DNA, electrophorese proteins, and sequence DNA.

To reduce immunogenicity, nerve grafts used in the subject invention can be made acellular by a variety of methods known to those of ordinary skill in the art. For example, the nerve tissue can be made acellular by freeze-killing, as described in the Materials and Methods section, or by chemical extraction with detergents (Sondell M et al. [1998] *Brain Res* 795:44-54). The nerve grafts can be rendered acellular before, during, or after application of one or more HSPG-degrading enzymes.

In Vitro Nerve Culture. The present invention also concerns methods of culturing nerve tissue for implantation into a human or animal. The culture methods of the subject invention can involve "predegenerating" the nerve tissue in vitro, which, following engraftment, improves the ability of regenerating axons to traverse the interface between the graft and host nerve tissue. For further detail refer to, for example, WO 2003/015612, which is incorporated herein by reference in its entirety. In this context, it should be understood that "predegenerating" includes applying HSPG-degrading enzymes (alone or in combination with other enzymes) to the graft.

The method of in vitro culture involves culturing the nerve tissue under conditions that permit the nerve tissue to grow in vitro and increase the neurite-promoting activity of the nerve tissue when subsequently implanted as a graft. The increase in neurite-promoting activity can be as determined by an in vitro neurite outgrowth assay of the nerve tissue.

Alternatively, an in vivo neurite outgrowth assay of the nerve tissue could also be utilized. Methods for assaying neurite outgrowth are known in the art and typically involve qualitatively or quantitatively determining the extent of neurite outgrowth on a solid support, such as a microplate or microscope slide. Standard fluorescence can be utilized.

The methods and compositions of the subject invention are applicable to nerve tissue of both the central nervous system (CNS) and peripheral nervous system (PNS). For example, nerve grafts of the subject invention can be used as interpositional nerve grafts in the PNS or as bridges in the brain and spinal cord and any extensions thereof. The damaged nerve or the nerve graft could be either peripheral nerve (e.g. sciatic, median, etc) or central nerve (e.g. spinal nerve, optic nerve etc).

The HSPG-degrading and CSPG-degrading enzymes used in the subject invention can be obtained from a variety of sources, including organisms that produce the enzyme naturally or organisms that produce (or overproduce) the enzyme through genetic modification (producing a recombinant enzyme). For example, the HSPG-degrading enzymes can be obtained from bacterial sources, including those that naturally produce the enzyme, or those that have been genetically modified to produce (or overproduce) the enzyme. HSPG-degrading enzymes can also be obtained from mammalian sources, including those mammals that naturally produce the enzyme or those mammals that have been genetically modified to produce (or overproduce) the enzyme. Alternatively, the HSPG-degrading enzyme can be chemically synthesized.

As used herein, the "proximal" part is intended to mean the part of the axon that remains in continuity with the neuron cell bodies or the part of the nerve containing these axons. The "distal" part is intended to mean the part of the axon that becomes disconnected from the neuron cell body or the part of the nerve containing these disconnected axons.

In the case of a peripheral nerve lesion, its proximal part is that which is connected to the ganglia or spinal cord. The distal part of the peripheral nerve is intended to mean the peripheral-most part of the nerve that is connected to the motor endplate (neuromuscular junction) or sensory organs. In the case of a lesion of the spinal cord, the proximal part is that which is in contact with nuclei or more anterior. The distal part is intended to mean that part which extends to a terminal synapse.

The terms "treating" or "treatment", as used herein, refer to reduction or alleviation of at least one adverse effect or symptom associated with the particular nerve damage suffered by the patient.

As used herein, the term "stem cell" is an unspecialized cell that is capable of replicating or self renewal, and developing into specialized cells of a variety of cell types.

As used herein, the term "progenitor cell" (also known as a "precursor cell") is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "co-administration" and variations thereof refers to the administration of two or more agents simultaneously (in one or more preparations), or consecutively.

As used herein, the term "biological activity" or "biologically active" is intended to refer to the activity associated with the particular agent, molecule, compound, etc.

Various vectors can be utilized to carry out genetic modification according to the subject invention. The vectors can be vaccine, replication, or amplification vectors.

Vectors utilized to carry out genetic modification can also comprise elements necessary to provide for the expression and/or the secretion of a polypeptide, such as a HSPG-degrading enzyme, or a biologically active fragment or variant thereof, encoded by the nucleotide sequences of the invention in a given host cell. Promoters which may be used to control expression are well known in the art. For further detail refer to, for example, WO 2003/015612, which is incorporated herein by reference in its entirety.

Materials and Methods

Animals—The experimental animals used were transgenic mice of the thy-1-YFP-H strain (Feng G, Mellor R H, Bernstein M, Keller-Peck C, Nguyen Q T, Wallace M, Nerbonne J M, Lichtman J W, Sanes J R [2000] "Imaging neuronal subsets in transgenic mice expressing multiple spectral variants of GFP" *Neuron* 28:41-51). In these mice, Yellow Fluorescent Protein (YFP) is expressed under the control of the thy-1 promoter. This promoter was chosen because the thy-1 gene product normally is expressed in the axons of motoneurons (Vidal M, Morris R, Grosveld F, Spanopoulou E [1990] "Tissue-specific control elements of the Thy-1 gene" *Embo J* 9:833-840). In the particular strain used (H), the YFP is expressed in only a subset of the axons in peripheral nerves, but when it is expressed, it fills the entire extent of the axonal domain (Feng et al., 2000, supra). These animals are used as heterozygotes and were obtained by breeding wild-type, C57B/6J females to heterozygous thy-1-YFP-H males (obtained from the Jackson Laboratories, Bar Harbor, Me.). Wild type animals in the $F_1$ generation of these matings that were used as tissue donors were litter mates of thy-1-YFP-H heterozygotes. All experiments were conducted on animals 2-6 months old. Animals were housed in the Animal Facilities at Emory University using guidelines approved by the Emory IACUC. All experiments were conducted in accordance with the Policy on the Use of Animals in Neuroscience Research of the Society for Neuroscience.

To investigate the makeup of the neurons whose axons are marked by the presence of YFP in these mice, we harvested spinal nerves and dorsal root ganglia from three untreated mice (five specimens were studied). Animals were euthanized with pentobarbital (150 mg/kg, IP) and perfused transcardially with a normal saline solution followed by periodate-lysate-paraforrnaldehyde fixative solution (McLean and Nakane, 1974). The L4 and L5 dorsal root ganglia were exposed by laminectomy and removed, along with their associated dorsal and ventral roots. The harvested tissues were placed on a microscope slide with the dorsal and ventral roots spread apart. A cover slip was then mounted on the slide using Vectashield (Vector Laboratories, Burlingame, Calif.).

To visualize YFP$^+$ axons in the dorsal and ventral roots, images were obtained from these whole mounts using confocal microscopy (Zeiss LSM-510). Stacks of optical sections 10 μm thick through the entire thickness of the specimen were obtained at relatively low magnification (10×). To capture the entire roots, stacks were obtained from several contiguous microscope fields. These images were then stitched together using Adobe Photoshop. Using these stacks of stitched images, the profiles of individual marked axons were identified and counted.

In three other mice, the $L_4$ and $L_5$ DRGs were harvested from euthanized and perfused animals, and serially sectioned at 40 μm thickness on a cryostat. All sections were mounted onto subbed slides and coversliped with Entellan (Electron Microscopy Sciences). Optical sections 2 μm thick were obtained at 63× magnification through the soma of each YFP$^+$ neuron. Sections containing identifiable nuclei were used to measure the cross sectional soma area of both the YFP$^+$ neuron and any other neurons in the field in which a nucleus was visible. Measurements were made using Image Pro-Plus software. The net result of this analysis was a determination of the soma size of all of the YFP$^+$ neurons in these ganglia and also the sizes of adjacent, YFP$^-$ neurons. Differences in mean soma sizes between these two groups were evaluated using an independent t-test.

Enzymes—Protease free chondroitinase ABC (from *Proteus vulgaris*, E.C. 4.2.2.4) was obtained from Seikagaku (Tokyo, Japan). Keratanase (E.C. 3.2.1.103), heparinase I (E.C. 4.2.2.7), and heparinase III (heparitinase) (E.C. 4.2.2.8) were obtained from Sigma-Aldrich (St. Louis, Mo.).

The chondroitinase ABC used was certified protease free but the other enzymes were not. To determine whether the keratanase, heparinase I, and heparinase III preparations we used are also free of proteases, we used the RediPlate 96 EnzChek Protease Assay kit from Molecular Probes (Eugene, Oreg.). This kit is capable of detecting a broad range of different proteases and was used in accordance with the manufacturer's directions. Each of the enzyme preparations was evaluated under conditions which were as close as possible to those used to treat nerve grafts. Reactions were performed in triplicate, using 2.5 μl of enzyme solution at a concentration of 80 Units/ml, for 2 hours at room temperature. Protease activity was read as fluorescence intensity. Any protease activity present in our enzyme preparations was compared to that of trypsin.

Nerve Repairs—In preliminary experiments with thy-1-YFP-H mice, we found that significant fluorescence persisted in the distal stumps of cut nerves for at least two weeks, making discrimination of regenerating YFP$^+$ axons from those that are undergoing anterograde degeneration impossible. Thus, all transected nerves in thy-1-YFP-H mice were repaired using a graft from a wild type litter mate. In all experiments, the wild type donor mouse was first anesthetized with pentobarbital sodium (90 mg/kg, IP). Once deeply anesthetized, the terminal branches of the sciatic nerves on both sides were exposed. The common fibular (CF) nerve was used in our experiments because in preliminary investigations, it was found that more YFP labeled neurons are found in this branch than in the tibial branch of the sciatic nerve. A segment of the CF nerve 3-5 mm long was then extracted, distal to the branch point of the CF nerve from the sciatic nerve. These grafts form a dark background against which we could observe regenerating axons and also provide a vehicle for the application of potential therapeutic treatments for enhancing regeneration. In most experiments, the left CF nerve graft from the wild type C57BL/6J mouse was soaked in 10 μl of normal saline at room temperature (23° C.) and placed on a marked cover slip in a plastic chamber to keep the saline from evaporating during the hour-long soak. The segment of the right nerve was treated in the same manner, but soaked in 10 μl of either chondroitinase ABC (20 U/ml), keratanase (20 U/ml), or heparinase I (20 U/ml) for one hour. After the nerves were removed, the wild type animal was euthanized. While the nerves were soaking, a thy-1-YFP-H mouse was anesthetized, and the CF nerves were exposed. The CF nerves on both sides of the animal were cut approximately 1 mm distal to their branch point from the sciatic nerve. The grafts from the wild type donor mouse were then inserted between the proximal and distal stumps and secured with fibrin glue. A 1:1 mixture of fibrin (E.C. 2325986) and fibronectin (E.C. 2891492) was paired with an equal amount of thrombin (E.C. 3.4.21.5). All of these reagents were obtained from Sigma-Aldrich. Once mixed together, the glue was applied to the site and allowed to set for at least 5 minutes. If the nerves were not properly aligned, or if the area was extremely moist, then re-gluing was necessary, but the surgical site was not closed until both the proximal and distal ends of the graft were securely fastened and properly aligned to the ends of the thy-1-YFP-H nerve. In a set of 11 additional mice, the CF nerves were cut and repaired as described above except that untreated grafts were used to repair the cut nerves bilaterally (n=3) or the grafts were treated bilaterally either with a solution of heparinase III (20 U/ml) (n=4) or with a mixture of equal volumes of all four enzymes (each 20 U/ml, starting concentration) (n=4) before being used to repair the cut nerves.

After a survival time of one week, the host mice were euthanized with pentobarbital sodium (150 mg/kg). The CF nerve area was exposed and fixed by immersion for 30 minutes with PLP solution. Once fixed, the CF nerve containing the graft was removed from the animal and placed on a microscope slide, as described above.

Axon profile tracing—Stacks of optical sections 10 μm thick through the entire thickness of the nerve were obtained using confocal microscopy, as described above. To capture the entire lengths of the regenerating axons, stacks were obtained from several contiguous microscope fields and stitched together using Adobe Photoshop. Using these stacks of stitched images, the profiles of individual regenerating axons were reconstructed in their entirety in the grafts. The length of these axon profiles, from the surgical repair site (proximal stump) to their distal ends was measured using Image Pro-Plus software. Axon profiles were measured in their entirety, even if they were represented in more than one optical section.

The number of axon profiles proximal to the surgical repair site was counted and compared to the number of axon profiles measured in the grafts in each animal studied. The ratio of those counts, the number of distal profiles per proximal profile, was calculated as a sprouting index. It is assumed that this index is a global measure of the amount of regenerative sprouting that had occurred in the one week survival period. The significance of differences in sprouting index in the different treatment groups was evaluated using analysis of variance (ANOVA), and appropriate post-hoc testing.

In all cases studied, the distributions of axon profile lengths were bimodal. This means that the significance of differences in axon profile length between control (saline-treated) and enzyme-treated nerves could not be evaluated readily using parametric statistical methods, such as t-tests or ANOVA, which assume the data in the different groups are normally distributed. Three measures of the significance of differences between treatment groups were evaluated. Differences in the distributions of lengths of axon profiles measured in untreated and saline- or enzyme-treated grafts were evaluated using a non-parametric statistical method (Kolmogorov-Smirnov (KS) two-sample test). This method tests the probability that the samples of axon profile lengths obtained from two groups were a part of the same population. In the bimodal distributions obtained, one mode represents axons that have regenerated very little; their lengths are nearly zero. As a second form of analysis, we effectively filtered these short axon profile lengths from the distribution before analysis, by considering only axon profiles that were longer than 500 μm. For the animals studied, the mean lengths of axon profiles >500 μm were normally distributed, and we evaluated the significance of differences between groups using a one-way ANOVA. Finally, we compared the proportions of all axon profile lengths studied that were longer than 500 μm. The distributions of these proportions in the different study groups also were normal, so that the significance of difference was evaluated using ANOVA. In both of these latter two comparisons, significant differences were found. Post-hoc testing was conducted in a pair wise manner to identify the sources of these significant differences. Because our sample sizes were relatively small (typically, N=3-6), we used the least conservative method (Fisher LSD) for all comparisons.

Immunohistochemistry—Chondroitinase ABC degrades the GAG side chains from the protein core of CSPGs, leaving small linking regions on the core protein once the GAG side chains have been digested away. These linking regions form a neo-epitope for antibodies recognizing either 4-sulfated (antibody 2B6) or 6-sulfated (antibody 3B3) chondroitin sulfate moieties (Caterson B, Christner J E, Baker J R, Couchman J R [1985] "Production and characterization of monoclonal antibodies directed against connective tissue proteoglycans" Fed Proc 44:386-393). Positive immunoreactivity using these antibodies thus forms an assay for complete CSPG degradation. We used this assay to investigate whether treatments of nerves with keratanase or either of the heparinases produced CSPG degradation. Antibody 3G10 recognizes a neo-epitope on the linking regions of HSPGs that is revealed after heparinase III, but not chondroitinase ABC or heparinase I digestion (David G, Bai X M, Van der Schueren B, Cassiman J J, Van den Berghe H [1992] "Developmental changes in heparan sulfate expression: in situ detection with mAbs" J Cell Biol 119:961-975). To determine whether our treatments with the different heparinases resulted in de-glycanation of HSPGs in the grafts used to repair cut peripheral nerves, we reacted tissue sections of segments of mouse CF nerve with heparinase I, heparinase III, chondroitinase ABC, or saline. As a positive control for 3G10 immunoreactivity, we treated a series of sections of mouse kidney in the same manner.

Segments of sciatic nerve 3-5 mm long were harvested from euthanized wild type mice and soaked, either in one of the four enzyme solutions or saline, as described above. They were then fixed in PLP for thirty minutes and stored in 10% sucrose solution until used for histology. Histological sections of the nerve segments were cut in either a longitudinal or coronal plane at a 10 μm thickness on a cryostat and mounted onto subbed slides. These sections were then incubated in buffer solution (0.1M Phosphate Buffer Solution (PBS), 2% Whole Goat Serum (WGS), and 0.03% Triton) for 1 hour at room temperature. Then the tissue was incubated either with antibody 3B3 or 2B6 at a dilution of 1:100, overnight at 4° C. Each slide was rinsed four times with 0.1M PBS with five minute intervals between each rinse. The sections were then incubated in a goat anti-mouse secondary antibody which was conjugated with the fluorophore, Alexa 594 (Molecular Probes, Eugene, Oreg.) at a dilution of 1:1000 for 30 minutes at room temperature. The slides were then cover slipped with Entellan, and viewed using the confocal microscope.

Following is an example which illustrates procedures, including the best mode, for practicing the invention. This example should not be construed as limiting. All percentages are by weight and all solvent mixture proportions are by volume unless otherwise noted.

EXAMPLE 1

Composition of Marked Axons in thy-1-YFP-H Mice

In the H strain of thy-1-YFP mice, a subset of axons in peripheral nerves is marked by the presence of yellow fluorescent protein (Feng G, Mellor R H, Bernstein M, Keller-Peck C, Nguyen Q T, Wallace M, Nerbonne J M, Lichtman J W, Sanes J R [2000] "Imaging neuronal subsets in transgenic mice expressing multiple spectral variants of GFP" Neuron 28:41-51), but the proportion of all axons marked, whether sensory or motor, is not known. The number of YFP+ axons were counted in the dorsal and ventral roots of the main segmental nerves (L4 and L5) which contribute to the CF nerve in optical sections (FIG. 1A) through whole mounts of spinal nerves from three mice (five sets of nerves). The mean numbers of sensory and motor axons (±SEM) are shown in Table I.

TABLE 1

Summary of YFP+ axons in spinal roots of thy-l-YFP-H mice
All values are means ± SEM

|  | Dorsal Root Axons |  | Ventral Root Axons |  | Total |
| --- | --- | --- | --- | --- | --- |
| L4 | 122.60 ± 15.29 | (58%) | 87.20 ± 16.23 | (42%) | 209.80 ± 31.49 |
| L5 | 74.00 ± 22.31 | (57%) | 55.40 ± 21.70 | (43%) | 129.40 ± 43.43 |
| Total | 196.60 ± 36.01 | (58%) | 142.60 ± 36.49 | (42%) | 339.20 ± 72.25 |

If the mean number of marked sensory axons in the L4 spinal nerve (122.6) is compared to the total number of neurons estimated in this ganglion, 4625, (Liebl D J, Tessarollo L, Palko M E, Parada L F [1997] "Absence of sensory neurons before target innervation in brain-derived neurotrophic factor-, neurotrophin 3-, and TrkC-deficient embryonic mice" Journal of Neuroscience 17:9113-9121), then approximately 2.6% of all sensory axons are marked. In both segmental nerves, significantly more sensory axons are marked by YFP fluorescence than are motor axons (t-test, p<0.001). Using the same approach as described above, the number of YFP+ axon profiles in CF nerves proximal to the lesions were counted. On average, 36.03 (±2.35 SEM) marked axons in each nerve were found; thus, it was assumed that we assume that 58% of them (21) are axons of DRG cells and 42% of them (15) are axons of motoneurons.

The cross sectional areas of YFP⁺ DRG neurons and of the non-fluorescent neurons surrounding them in tissue sections through the $L_4$ and $L_5$ ganglia were counted. All measurements were made on profiles of cells containing a nucleus. The distributions of soma cross sectional areas of YFP⁺ and YFP⁻ DRG neurons are shown in FIG. 1B. In both groups of cells, both large and small neurons were encountered, but the distribution of YFP⁺ cells contains more larger and fewer small cells than that of the surrounding YFP⁻ neurons. The mean size of the YFP⁺ neurons is significantly (t test, $p<0.01$) larger than the mean size of the YFP⁻ cells (FIG. 1B, right).

EXAMPLE 2

Axon Regeneration in the thy-1-YFP-H Mouse

Figure 2:
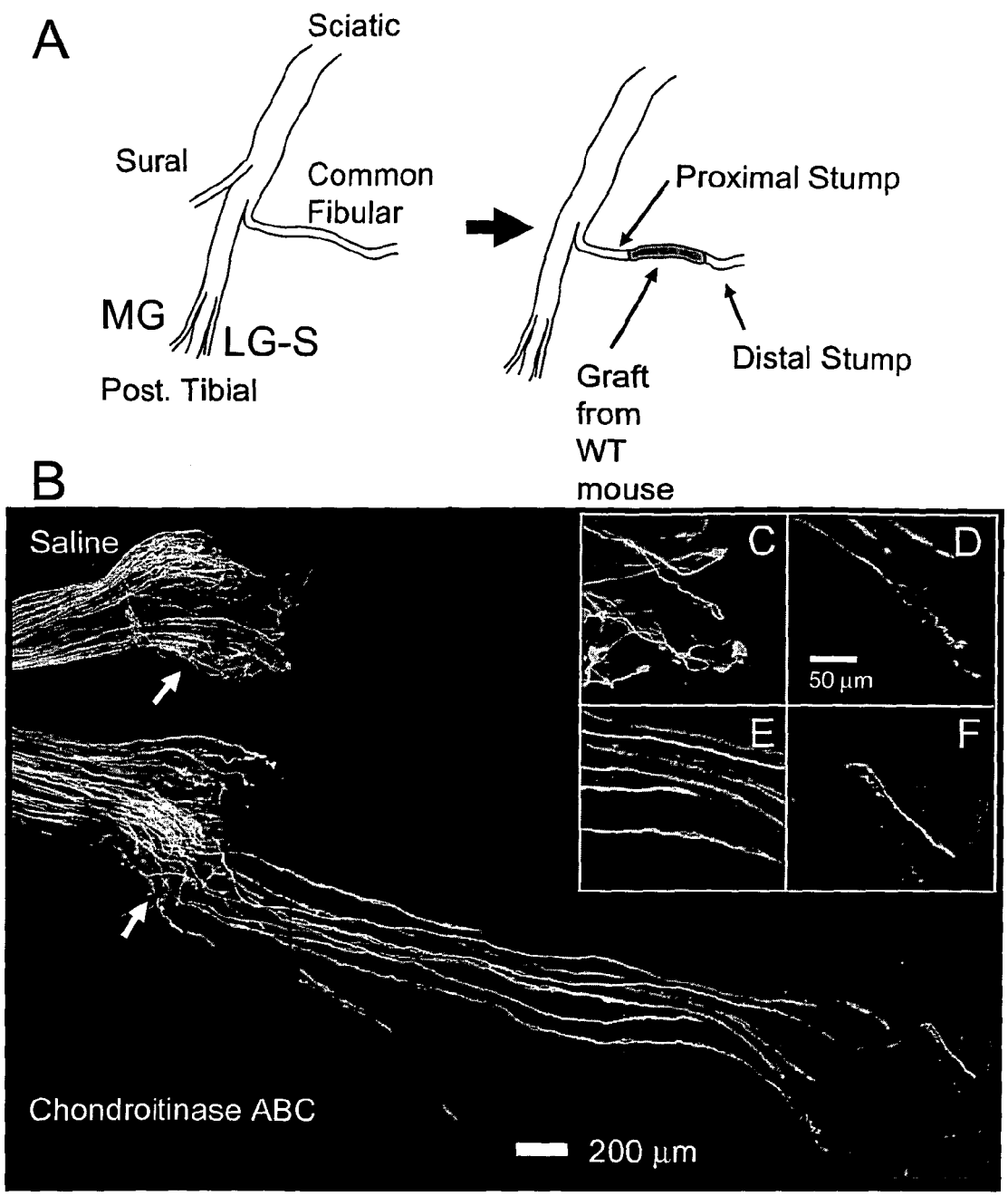
FIGS. 2A-2F.
Figure 3:
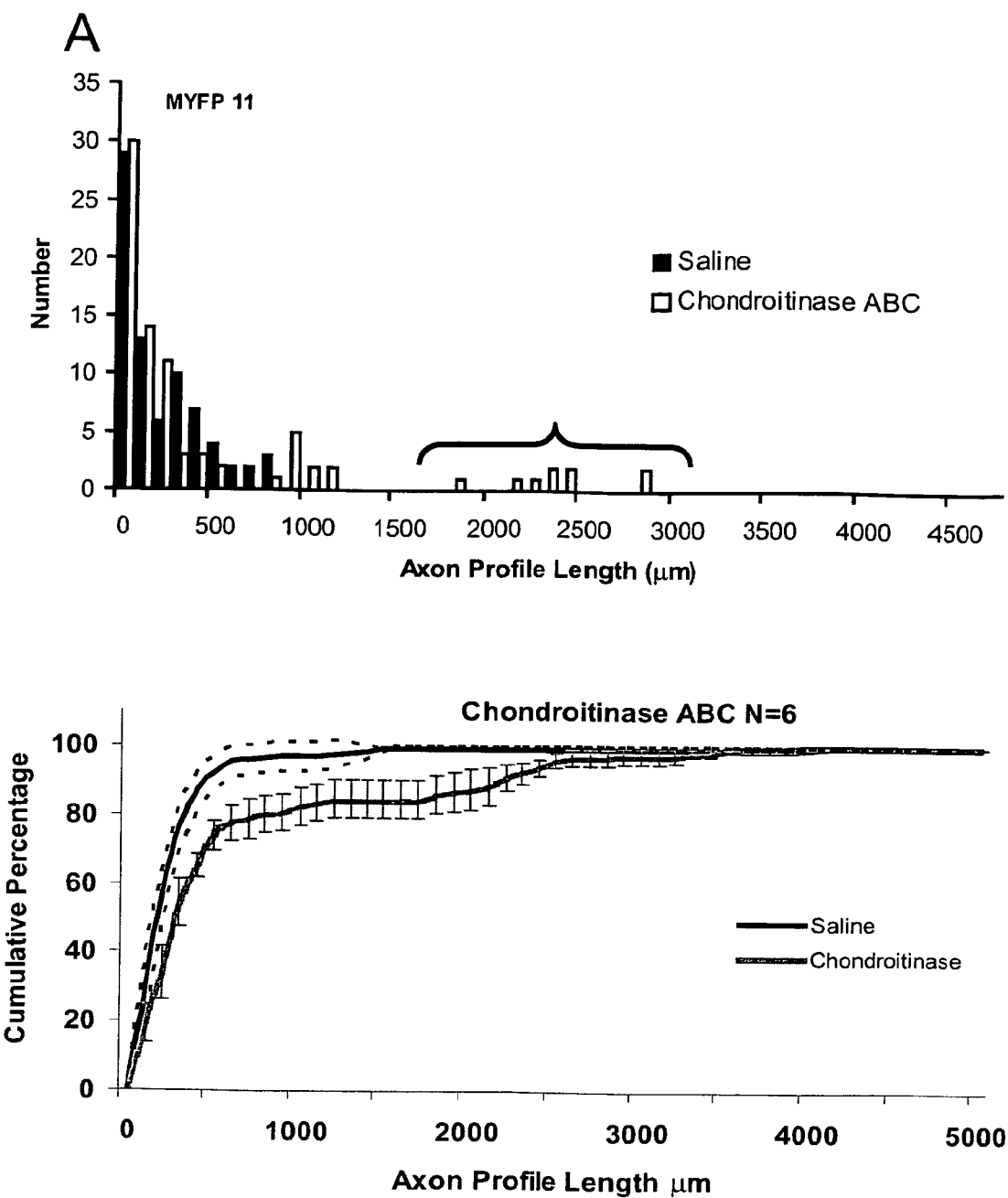
FIGS. 3A-3B.

In thy-1-YFP-H mice one week after repairing a surgical transection of the CF nerve with an untreated or saline-treated graft from a wild type littermate (FIG. 2A), little evidence for axon regeneration is noted (FIG. 2B: Saline). One week after nerve repair, most of the fluorescent profiles of the marked axons are found close to the surgical repair site, the interface between the proximal stump of the cut nerve and the graft. A few axons have penetrated the graft and have grown into it, but most axon profiles observed have not. This lack of growth of axons into untreated grafts is reflected in the distribution of the measured lengths of axon profiles (FIG. 3A). Greater than 90% of fluorescent axon profiles in these nerves were shorter than 500 µm.

EXAMPLE 3

Chondroitinase ABC Treatment Enhances Axonal Regeneration

In thy-1-YFP-H mice one week after repairing the cut CF nerve with a graft from a wild type mouse which had been treated with chondroitinase ABC, the outcome is quite different (FIG. 2B, Chondroitinase ABC). Whereas, most of the axon profiles in saline-treated or untreated grafts ended in large flat endings which resemble either lamellopodia-containing growth cones or retraction bulbs (FIG. 2C), the endings of axon profiles that had entered and grown into the chondroitinase-treated grafts were more fusiform (FIGS. 2D-F). Many more fluorescent axons are found to have grown into the graft, some for considerable distances. This observation is reflected in the distribution of the lengths of profiles of fluorescent regenerating axons. As shown in FIG. 3A, which is a histogram of measurements of axon profile lengths from the left and right nerves of a single mouse, many axon profile lengths in both saline-treated and chondroitinase ABC-treated grafts are very short.

A second population of longer axon profile lengths was found only in the chondroitinase-treated graft of this mouse (brackets). These differences between axon profile lengths in saline-treated and chondroitinase ABC-treated grafts are noted also in the cumulative frequency distributions based on analysis of six mice shown in FIG. 3B. In this graph the shift to the right (or downward) of the data for the chondroitinase ABC-treated nerves means that, for any given axon profile length, proportionately more axon profiles are that length or longer when encountered in chondroitinase ABC-treated grafts. When compared using a non-parametric statistical test, the distributions of axon profile lengths measured in chondroitinase ABC-treated and in saline-treated grafts are significantly different (KS, $p<0.001$).

EXAMPLE 4

Heparinase, but not Keratanase Treatments Enhance Axonal Regeneration

The GAGS on HSPGs consist of polymers of a disaccharide composed of hexuronic acid (either D-glucuronic acid (GlcA) or its epimer, L-iduronic acid (IdoA)) and D-glucosamine (GlcN). The GlcN residues in heparin are predominantly N-sulfated, whereas those in heparan are more varied, being both N-acetylated and N-sulfated (Lindahl U, Kusche-Gullberg M, Kjellen L (1998) "Regulated diversity of heparan sulfate" *J Biol Chem* 273:24979-24982). Two different bacterial heparin lyases were used to degrade GAGs on HSPGs. Both break the α-1, 4 linkages between sugar pairs. Heparinase I is most effective in breaking glycosidic linkages in heavily sulfated saccharides, such as heparin. It also can remove the less sulfated heparan sulfate-containing GAG side chains of HSPGs, but heparinase III is much more effective in doing so (Desai U R, Wang H, Linhardt R J [1993] "Substrate specificity of the heparin lyases from *Flavobacterium heparinum* " *Arch Biochem Biophys* 306:461-468).

Figure 4:
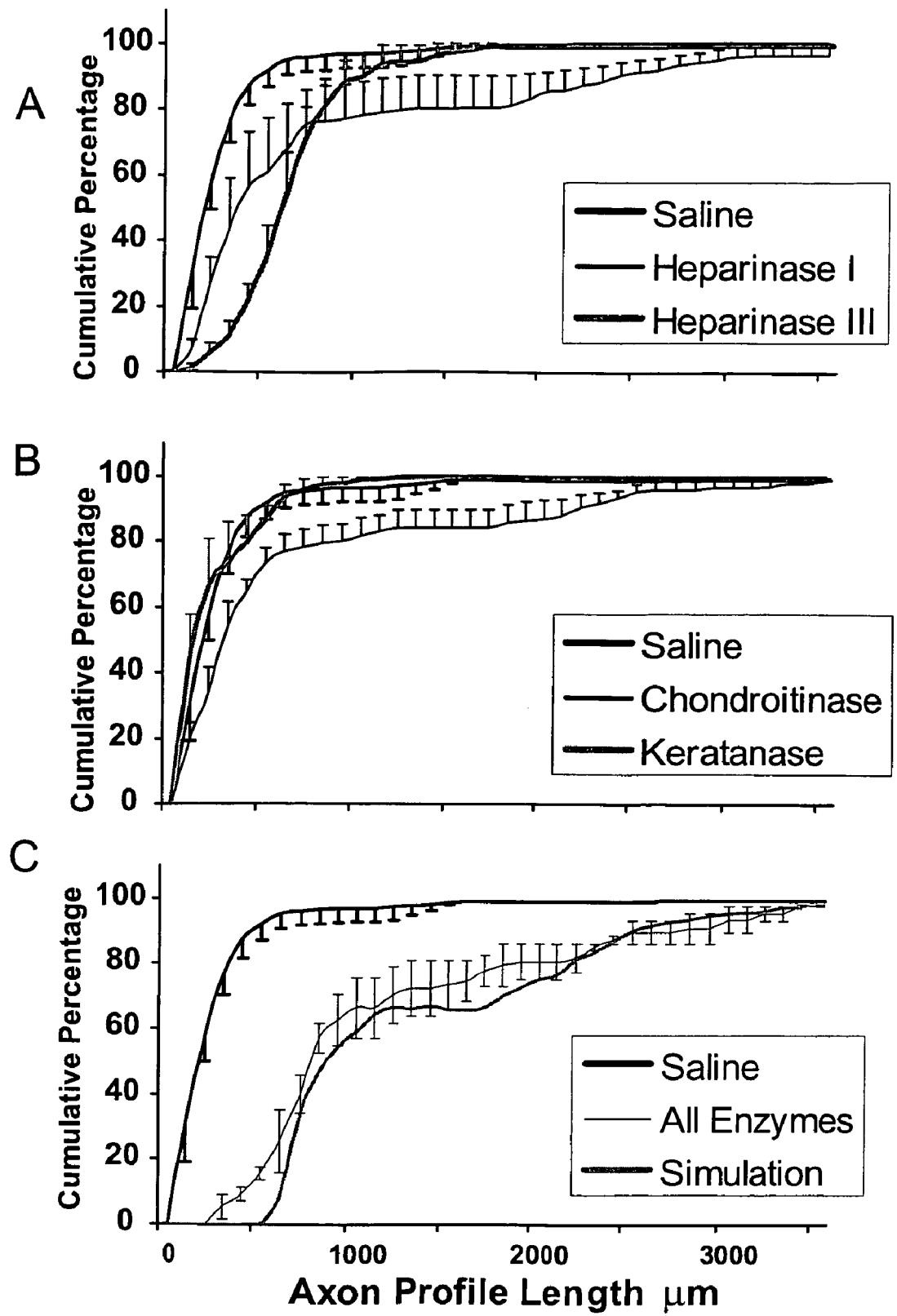
FIGS. 4A-4C. Cumulative frequency distributions of lengths of axon profiles are shown for nerves repaired (A) using saline-treated grafts (heavy line) and grafts treated with heparinase I (thin black line), or heparinase III (thin grey line), or (B) chondroitinase ABC (thin black line), or keratanase (thin grey line).

The distributions of axon profile lengths measured in heparinase I- and heparinase III-treated grafts are shown in FIG. 4A. These distributions are significantly different from that of axon profile lengths measured in saline-treated grafts (KS, $p<0.01$).

Keratanase treatment of nerve grafts was used to remove the GAG side chains of any KSPGs in the pathway of regenerating axons. The distributions of lengths of regenerating axon profiles measured in saline-treated and keratanase (20 U/ml)-treated grafts are shown in FIG. 4B. Unlike the results following treatment with either CS or HS degrading enzymes, differences in these distributions following keratanase treatment were not statistically significant (KS, $p<0.35$).

EXAMPLE 5

Treatments with Enzyme Mixture

Four nerve grafts were treated with a mixture of the same concentrations of all four enzymes (heparinase I, heparinase III, chondroitinase ABC, and keratinase) before using them to repair cut CF nerves. The results of analysis of axon profile lengths in these animals are shown in FIG. 4C. Treatment with a mixture of the different enzymes resulted in a change in the distribution of axon profile lengths that is significantly greater ($p<0.01$) than that found in saline-treated grafts and also from that found in the grafts treated with any one of the enzymes by itself.

The change in the distribution of axon profile lengths that would be produced by the arithmetic sum of the individual treatments was estimated. For each treatment, the percent change in the distribution of axon profile lengths, relative to that observed with saline-treated grafts was determined. These percent differences were then summed and subtracted them from the distribution of axon profile lengths measured in saline-treated grafts to generate a simulated distribution of axon profile lengths. When the summed percentage was greater than the corresponding value in the distribution of axon profile lengths measured in saline-treated grafts, the value in the simulated distribution was set to zero. The resulting simulated distribution is shown by the grey line in FIG. 4C. Note that this simulated distribution falls nearly entirely within the 95% confidence limits of the distribution of axon profile lengths measured in grafts treated with the mixture of enzymes.

EXAMPLE 6

Comparison of the Effects of Different Enzyme Treatments on Axonal Regeneration

Figure 5:
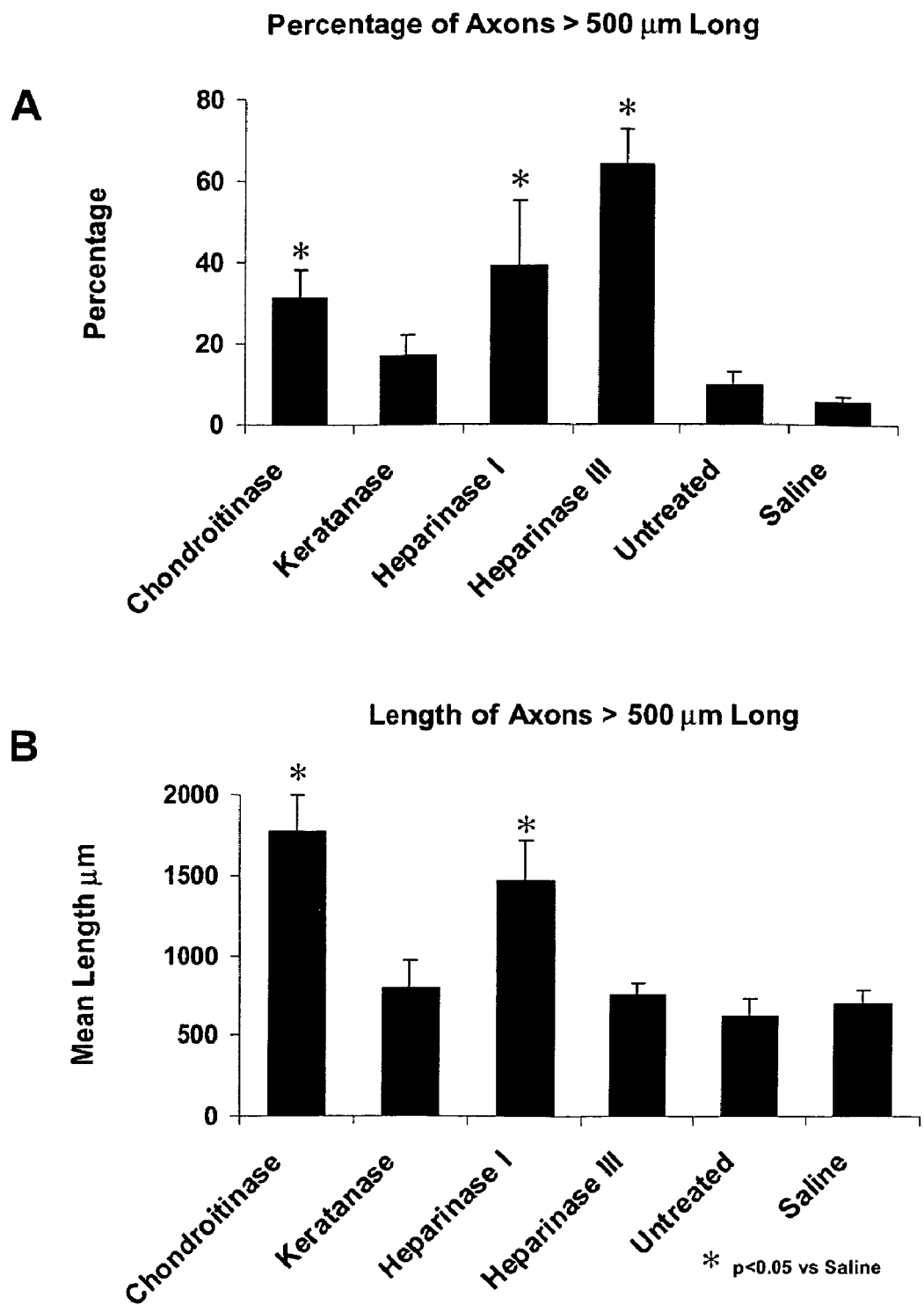
FIGS. 5A-5B. Two measures of the relative efficacy of different treatments are shown.

The proportion of axon profiles that had extended longer than 500 μm into grafts was significantly greater when the graft was soaked in chondroitinase ABC, heparinase I, or heparinase III than if the graft was incubated in saline or keratanase or not incubated at all (FIG. 5A). On average, only 5.64% (±2.37, SEM) of axon profiles measured in saline-treated grafts extended further than 500 μm from the proximal repair site, as compared to 31.28% (±6.06) of axon profiles in chondroitinase ABC-treated grafts (Fisher LSD, p<0.017). These differences were also significantly greater than the percentage of axon profile lengths >500 μm measured in three untreated grafts (9.55% ±3.69) (LSD, p<0.05). On average, in the keratanase treated grafts, only 15.64% (±2.37, SEM) of all of the axon profiles were longer than 500 μm (LSD, p<0.51). Significantly greater proportions of axon profile lengths >500 μm were measured in the heparinase I-treated grafts, (38.93% ±16.51, SEM) (LSD, p<0.007), and the heparinase II-treated grafts (63.96% ±8.74 SEM) (LSD, p<0.0001).

Treatment of grafts with the mixture of enzymes promoted the elongation of nearly four times as many regenerating axons to a length exceeding 500 μm as found after treatment with chondroitinase ABC (p<0.0005), and nearly twice as many as found after heparinase I treatment (p<0.007). Heparinase III treatment resulted in proportionally more axon profiles longer than 500 μm than either chondroitinase ABC (p<0.01) or heparinase I (p<0.05) treatments.

The mean lengths (±SEM) of axon profiles longer than 500 μm in the different treatment groups is shown in FIG. 5B. Among those axons that extended longer than 500 μm into the graft, those growing into chondroitinase-treated grafts were almost three times longer (1766.22 μm±171.19, SEM) than the average length of the axons that had regenerated into the grafts treated with saline (662.40 μm±191.83) (LSD, p<0.002) or untreated grafts (619.62 μm±110.34) (LSD, p<0.009). In heparinase I-treated grafts, the mean length of axon profiles longer than 500 μm (1466.93 μm+250.85 SEM) was significantly greater than that observed in saline-treated (p<0.04) or untreated (p<0.01) grafts, but not significantly different from that observed in grafts treated with chondroitinase ABC. In contrast, the mean lengths of axon profiles longer than 500μm in keratanase-treated (800.28 μm±170.83, SEM) (LSD, p<0.39) or heparinase III treated grafts (755.89 μm+75.67 SEM) were not significantly different from those measured in saline-treated (p<0.71) or untreated grafts (p<0.67). In grafts treated with the enzyme mixture, the mean length of axon profiles longer than 500 μm was significantly greater than that observed in saline-treated (p<0.05) or untreated (p<0.01) grafts, but not significantly different from that observed in grafts treated with either chondroitinase ABC or heparinase I.

EXAMPLE 7

Enzyme Effects on Regenerative Sprouting

Figure 6:
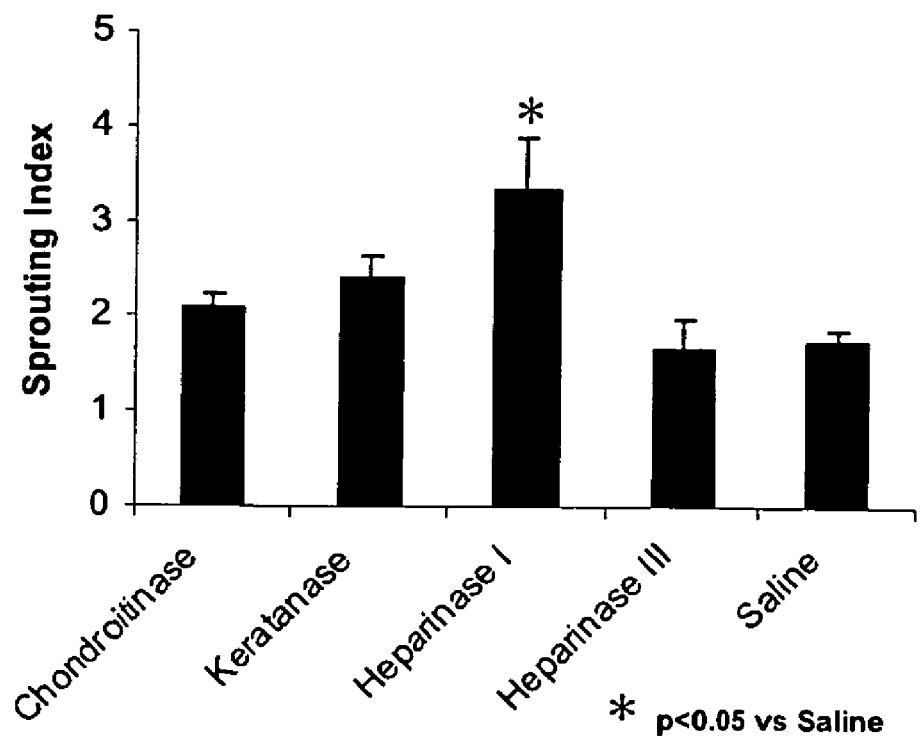
FIG. 6. We counted the number of YFP$^+$ axon profiles above the lesion site in the CF nerve (proximal count) and compared this to the total number of axon profiles measured in grafts (distal count). The ratio of distal count to proximal count is an index of the amount of regenerative sprouting (sprouting index), and represents a global average (±SEM) of the number of sprouts per axon.

Axons in the proximal stump of cut peripheral nerves form sprouts as one of the earliest aspects of regeneration. One way in which proteoglycan de-glycanation could affect axon regeneration is by stimulating the formation of such regenerative sprouts. To assay for this possibility, the number of YFP$^+$ axon profiles in the CF nerve proximal to the nerve transection in each animal was counted and this count was compared to the number of axon profiles measured in the grafts. The latter includes all axon profiles that could be measured distal to the surgical repair site, even if those profiles were very short. The ratio of the distal counts to the proximal counts is a sprouting index. Mean sprouting indices (±SEM) for the different treatment groups are shown in FIG. 6. No significant differences were found between most of the groups, but in the nerve grafts treated with heparinase I, nearly twice as many branches of axons were found as the other groups (LSD, p<0.01).

EXAMPLE 8

Specificity of Chondroitinase ABC and Heparinase treatments

Figure 7:
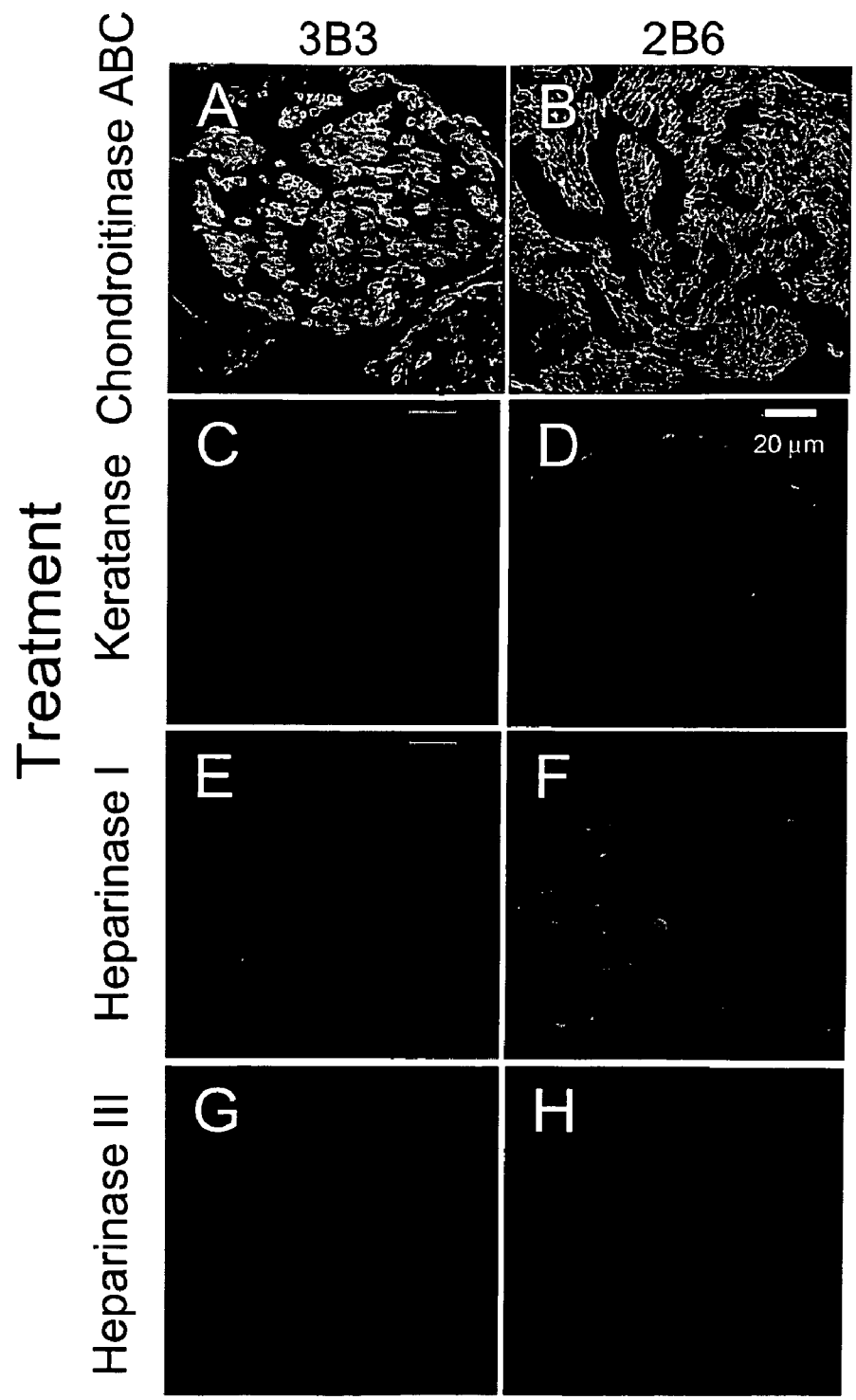
FIGS. 7A-H. We used antibodies to neo-epitopes, epitopes revealed only after enzyme treatment, to investigate whether the effects of the treatments of nerve grafts with enzymes could be attributed to the removal of GAGs from CSPGs. Antibodies 3B3 and 2B6 recognize "stubs" which remain after extensive chondroitinase ABC digestion. Histological cross sections of common fibular nerves which had been reacted in situ with different enzymes were incubated on slides with either of these antibodies. Each Figure (A-H) displays the result of a different combination of pre-treatments and antibody binding. All figures shown are at the same magnification.

When chondroitinase ABC activity has resulted in the removal of GAG side chains from CSPGs, the antibodies 3B3 and 2B6 will bind to neo-epitopes at the GAG attachment sites on the core glycoproteins of CSPGs that are created by the de-glycosylating activity of the enzyme (Caterson B, Christner J E, Baker J R, Couchman J R [1985] "Production and characterization of monoclonal antibodies directed against connective tissue proteoglycans" *Fed Proc* 44:386-393). Positive immunoreactivity to both of these antibodies was found in the locations of endoneurial tubes in sections from peripheral nerves which had been treated in situ with chondroitinase ABC (FIG. 7:A, B). This immunoreactivity was found throughout the entire nerve section. No immunoreactivity (i.e. no chondroitinase activity) was observed in sections from nerves soaked in saline, keratanase (FIG. 7: C, D), heparinase I (FIG. 7: E, F), or heparinase III (FIG. 7: G, H). Thus the growth promoting effects of heparinase I and heparinase III treatments described above were not because these enzymes induced the de-glycanation of CSPGs in the grafts.

Similarly, antibody 3G10 binds to a neo-epitope that is revealed by heparinase III treatment, but not chondroitinase ABC or heparinase I treatments (David G, Bai X M, Van der Schueren B, Cassiman J J, Van den Berghe H [1992] "Developmental changes in heparan sulfate expression: in situ detection with Abs" *J Cell Biol* 119:961-975). Sections of mouse CF nerves were treated with saline, chondroitinase ABC, heparinase I, or heparinase III at identical concentrations and under identical conditions to those used to treat nerve grafts. The sections were then processed using antibody 3G10. Results of this experiment are shown in FIG. 8.

Figure 8:
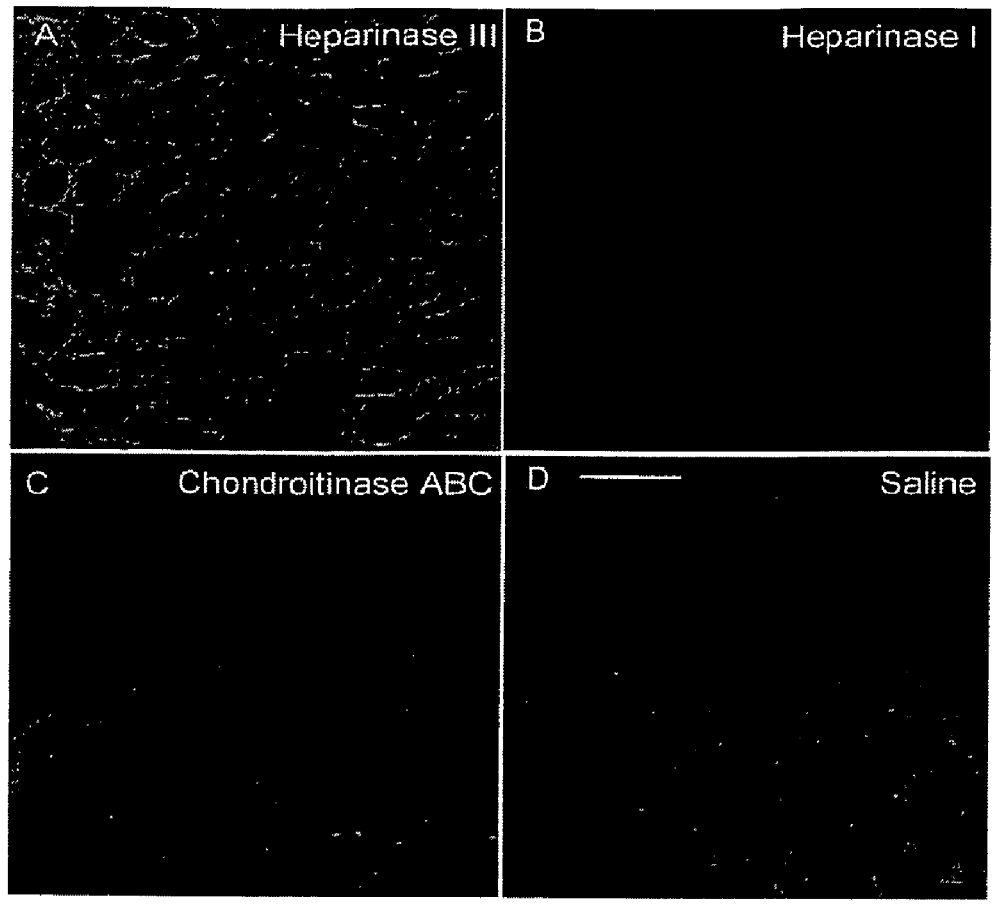
FIGS. 8A-8D. Heparinase III treatments remove HSPG GAGs.

After treatment with heparinase III, marked immnunoreactivity to antibody 3G10 is found in nerves in the regions of the endoneurial tubes (FIG. 8: A). The same was found in sections treated with heparinase III after chondroitinase ABC treatment. In sections treated with heparinase I, no immunoreactivity to 3G10 was found (FIG. 8: B), as was noted in sections pre-treated in either chondroitinase ABC or saline (FIG. 8: C, D).

All patents, patent applications, provisional applications, and publications referred to or cited herein are incorporated by reference in their entirety, including all Figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method for promoting axonal outgrowth from a damaged nerve, wherein said method comprises applying at least one heparan sulfate proteoglycan-degrading enzyme to the damaged nerve, wherein the method comprises:
   a) coapting proximal and distal stumps, of a severed nerve, either directly or through a nerve graft or conduit, and applying the enzyme to the severed nerve; or
   b) applying the enzyme directly to a nerve that has been damaged but not completely severed; wherein the heparan sulfate proteoglycan-degrading enzyme is selected from the group consisting of heparinase I, heparinase III, and heparanase, and is applied to the damaged nerve at a concentration sufficient to cause axonal outgrowth.

2. The method, according to claim 1, wherein said enzyme is heparinase I or heparinase III.

3. The method, according to claim 1, wherein said enzyme is heparinase I.

4. The method, according to claim 1, further comprising administering at least one other glycosaminoglycan (GAG)-degrading enzyme to the nerve.

5. The method, according to claim 1, further comprising administering to the nerve at least one chondroitin sulfate proteoglycan-degrading enzyme selected from the group consisting of chondroitinase ABC, chondroitinase A, chondroitinase C, and chondroitinase AC.

6. The method, according to claim 1, further comprising administering to the nerve at least one keratan sulfate proteoglycan-degrading enzyme.

7. The method, according to claim 6, wherein said keratin sulfate proteoglycan-degrading enzyme is keratanase or endo-b-galactosidase.

8. The method according to claim 1, wherein said method further comprises co-applying a tissue adhesive to the damaged nerve.

9. The method according to claim 1, wherein said method further comprises applying a growth factor or trophic factor to the damaged nerve.

10. The method according to claim 1, wherein the damaged nerve is a damaged peripheral nerve.

11. The method according to claim 1, wherein the damaged nerve is a damaged central nerve.

12. The method according to claim 1, wherein the damaged nerve is human.

13. A method for promoting axonal outgrowth from a severed nerve, wherein said method comprises coapting proximal and distal stumps of the severed nerve, either directly or through a nerve graft or conduit, and applying to the severed nerve a heparan sulfate proteoglycan-degrading enzyme selected from the group consisting of heparinase I, heparinase III, and heparanase, wherein said enzyme is applied to the nerve at a concentration sufficient to cause axonal outgrowth.

14. The method, according to claim 13, wherein said enzyme is heparinase I.

* * * * *

UNITED STATES PATENT AND TRADEMARK OFFICE
CERTIFICATE OF CORRECTION

PATENT NO. : 7,772,185 B2  Page 1 of 1
APPLICATION NO. : 11/051996
DATED : August 10, 2010
INVENTOR(S) : Arthur W. English, Robert McKeon and Erica Werner It is certified that error appears in the above-identified patent and that said Letters Patent is hereby corrected as shown below:

Column 12,
Line 61, "paraforrnaldehyde" should read --paraformaldehyde--

Column 19,
Line 26, "heparinase II-treated" should read --heparinase III-treated--

Column 20,
Line 45, "with Abs"" should read --with mAbs"--
Lines 51-52, "immnunoreactivity" should read --immunoreactivity--

Signed and Sealed this

Sixteenth Day of November, 2010

David J. Kappos
*Director of the United States Patent and Trademark Office*